(12) United States Patent
Cavazza

(10) Patent No.: US 6,180,680 B1
(45) Date of Patent: Jan. 30, 2001

(54) PHARMACEUTICAL COMPOSITIONS COMPRISING ALKANOYL L-CARNITINE IN COMBINATION WITH A STATINE FOR TREATING PATHOLOGIES BROUGHT ABOUT BY AN ALTERED LIPID METABOLISM

(75) Inventor: Claudio Cavazza, Rome (IT)

(73) Assignee: Sigma-Tau Industrie Farmaceutiche Riunite S.p.A., Rome (IT)

( * ) Notice: Under 35 U.S.C. 154(b), the term of this patent shall be extended for 0 days.

(21) Appl. No.: 09/446,806

(22) PCT Filed: Jun. 18, 1998

(86) PCT No.: PCT/IT98/00163

§ 371 Date: Dec. 28, 1999

§ 102(e) Date: Dec. 28, 1999

(87) PCT Pub. No.: WO99/01126

PCT Pub. Date: Jan. 14, 1999

(30) Foreign Application Priority Data

Jul. 1, 1997 (IT) ............................................. RM97A0390

(51) Int. Cl.$^7$ ............................. A61K 31/14; A61K 31/35
(52) U.S. Cl. ............................ 514/642; 514/451; 514/460
(58) Field of Search ..................................... 514/642, 451, 514/460

(56) References Cited

PUBLICATIONS

Database Medline US National Library of Medicine (NLM), Savica V et al: "The hypotriglyceridemic action of the combination of L–carnitine+simvastatin vs. L–carnitine and vs. Simvastatin!" XP002081551 see abstract & Clin Ter, Jan. 1992, 140 (1 Pt 2) P17–22, Italy.

*Primary Examiner*—Theodore J. Criares
*Assistant Examiner*—Jennifer Kim
(74) *Attorney, Agent, or Firm*—Nixon & Vanderhye

(57) ABSTRACT

Coordinated use of an alkanoyl L-carnitine such as propionyl L-carnitine and a statin such as simvastatin is described for treating pathologies resulting from altered lipid metabolism. Coordinated use of the two ingredients is achieved by substantial contemporaneous co-administration of the two active ingredients or by administering a combination composition containing a mixture of the two active ingredients.

2 Claims, No Drawings

PHARMACEUTICAL COMPOSITIONS COMPRISING ALKANOYL L-CARNITINE IN COMBINATION WITH A STATINE FOR TREATING PATHOLOGIES BROUGHT ABOUT BY AN ALTERED LIPID METABOLISM

The present invention relates to a pharmaceutical composition for the prevention and treatment of cardiovascular diseases caused by abnormal lipid metabolism.

Cardiovascular diseases related to abnormal lipid metabolism are very frequent in industrialised countries. In Italy, for instance, they account for more than 40% of the overall mortality (Capocaccia R., Farchi G., Prati S. et al.: La mortalità in Italia nell'anno 1989. Rapporto ISTISAN 1992/22). Our knowledge of the relationships between cholesterol and coronary heart disease stem from epidemiological studies conducted over the past few years. The conclusions reached in these studies indicate that the development of severe coronary atherosclerosis and coronary heart disease are closely correlated with serum cholesterol levels (McGill H. C. Jr. et al.: The International Atherosclerosis Project. Lab. Invest. 18: 463–653, 1968; Keys A.: Seven Countries: Death and Coronary Heart Disease. Harvard University Press, Cambridge, 1980).

Correction of eating habits through suitable diet is invariably the first measure adopted in cases of hyperlipidaemia. Satisfactory results are not always achieved, however, owing to widespread intolerance of strict dietary discipline, to the severity of the hypercholesterolaemia, or to genetic-type resistance.

To achieve the desired results in these patients, i.e. normalisation of blood levels of triglycerides and cholesterol, pharmacological treatment has to be resorted to. Hypolipaemic drugs fall into two categories: those which above all reduce cholesterol and those which mainly reduce triglycerides.

The former group of drugs includes the statins, probucol and resins, while the latter group includes the fibrates, nicotinic acid and fatty acids belonging to the omega-3 series.

The statins (lovastatin, sinvastatin, provastatin, fluvastatin, and the like) are inhibitors of hydroxy-methyl-glutaryl-coenzyme A (HMG-CoA) reductase. By inhibiting this enzyme, they reduce the hepatic synthesis of cholesterol (Lancet 1994; 334: 1383–1389). To compensate for the reduction of intracellular cholesterol the liver cell produces several receptors for LDL and VLDL lipoproteins, which are thus removed from the bloodstream.

The statins also give rise to reduced intestinal absorption of cholesterol of dietary origin and to a reduced output of apoprotein B present in low-density lipoproteins (LDL).

The statins are drugs which are better tolerated than the other anticholesterolaemic agents, but are not without drawbacks, the side effects most commonly induced by these drugs being gastrointestinal disorders, skin rashes and headache.

A number of patients have also reported sleep disorders (E J Schaffer, N Engl J Med, 319; 1222, 1988; Lancet, 339: 547, 29 February 1992), while, in 1–2% of patients taking high doses of statins, an at least 3-fold increase in plasma aminotransferase activity has been noted compared to baseline values, which may even require discontinuation of the treatment.

In addition, it has been reported that though the statins lead to a reduction in the number of deaths due to coronary heart disease, an increase has been observed, in treated patients, of deaths caused by other events such as tumours or trauma (Davey-Smith G., Song F., Sheldon T. A.: Cholesterol lowering and mortality: the importance of considering initial level at risk. BMJ, 1993; 306: 1367–1373; Ravnshov U.: Cholesterol lowering trials in coronary heart disease: frequency of citation and outcome. BMJ 1992; 305: 15–19). The results of experiments in animals and human subjects have suggested that, to reduce cholesterol levels, pharmacological treatment with statins should be given only to patients at high risk for coronary disease in the short term (JAMA, 1996; 275: 55–60).

Equally well known is the antitriglyceridaemic and anticholesterolaemic effect of a number of alkanoyl carnitines, particularly acetyl L-carnitine. U.S. Pat. No. 4,268.524 describes a therapeutic method for increasing high-density lipoprotein (HDL) levels so as to selectively reduce the HDL:(LDL+VLDL) ratio in the plasma of patients at risk for cardiovascular disease, in which this ratio is abnormally high; the method comprises administering 5–50 mg/kg/day of alkanoyl carnitine or one of its pharmacologically acceptable salts.

It has now been found, unexpectedly, that the co-ordinated use—this term being defined precisely here below—of an alkanoyl L-carnitine in which the linear or branched alkanoyl has 2–6 carbon atoms, or of one of its pharmacologically acceptable salts, and a statin enables an enhanced effect on the anticholesterol aemic and antitriglyceridaemic action to be achieved as compared to the separate, independent administration of the two active ingredients. This enables the same therapeutic results to be achieved using lower doses of statins, thus making for a marked reduction in their toxic and side effects.

The well-known lack of toxic and side effects of the alkanoyl L-carnitines and the use of lower doses of statins as compared to the routine doses (10–40 mg/day) makes the co-ordinated use as per the invention particularly useful and safe both for the treatment of hypercholesterolaemic and/or hknpertriglyceridaemic patients at high risk for cardiovascular disease in the short, medium or long term and for the prevention of such diseases.

As a result of the above-mentioned synergistic effect, it has been found, in fact, that the statin dose can be reduced to 5–20 mg/day, whereas the alkanoyl L-carnitine dose can be reduced to 2–30 mg/kg/day.

According to the present invention, what is meant by "coordinated use" of the afore-mentioned compounds is either their co-administration, i.e. the substantially simultaneous administration of one of the aforesaid alkanoyl L-carnitines, or one of their pharmacologically acceptable salts, and of a statin, or, indifferently, the administration of a composition comprising a combination or mixture of the aforesaid active ingredients, optionally in addition to suitable excipients.

The scope of the present invention encompasses therefore both the co-administration of one of the aforesaid alkanoyl L-carnitines, or one of their pharmacologically acceptable salts, together with a statin, and orally or parenterally administrable pharmaceutical compositions, comprising a mixture of the two active ingredients.

Preferably the statin is selected from the group comprising lovastatin, simvastatin, provastatin and fluvastatin, while the alkanoyl L-carnitine is selected from the group comprising acetyl, propionyl, butyrl, valeryl and isovaleryl L-carnitine or one of their pharmacologically acceptable salts.

Even more preferably, the statin is simnvastatin and the alkanoyl L-carnitine propionyl L-carnitine or one of its pharmacologically acceptable salts.

What is meant by pharmacologically acceptable salt of an alkanoyl L-carnitine is any salt of the latter with an acid that does not give rise to unwanted toxic or side effects.

These acids are well known to pharmacologists and to experts in pharmacy.

Non-limiting examples of pharmacologically acceptable salts of alkanoyl L-carnitines are chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

One preferred composition, in unit dosage form, is a composition comprising statin 5–10 mg and alkanoyl L-carnitine 100–1000 mg.

The enhanced effect of alkanoyl L-carnitine and statin has been confirmed, for example, by the results of a clinical study which are given here below.

Clinical Study

Eight hypertriglyceridaemic patients (3 males and 5 females) were recruited for the study, with a mean age of 65 years (range: 52–70), presenting mean triglyceridaemia values of $213.0 \pm 21.18$ mg % and mean cholesterolaemia values of $158.1 \pm 25.90$ mg %, who were put on a dietary regimen consisting in 40 Kcal/kg, 1.2 g/kg proteins and 1.4 g/kg lipids daily.

After baseline determinations of cholesterolaemia, triglyceridaemia, bilirubinaemia, alkaline phosphatase, protidaemia, GOT and GPT, all subjects took propionyl L-carnitine 2 g/day os for 60 days, which was discontinued on day 61 for a 30-day wash-out period. Simvastatin was then administered at a dose of 10 mg/day os in the evening for 30 days, followed by a further 30-day wash-out period and then by another 30-day period during which propionyl L-carnitine 1.5 g/day os and simvastatin 5 mg/day os were administered simultaneously.

Blood-chemistry tests were performed before and after each course of drug treatment and at the end of each wash-out period. The data obtained were subjected to statistical analysis using Student's t-test for paired data (Table 1).

TABLE 1

Experimental protocol/baseline study

| Treatment with propionyl L-carnitine 2 g/day os | Wash-out | Treatment with simvastatin 10 mg/day os | Wash-out | Treatment with propionyl L-carnitine 1.5 g/day os + simvastatin 5 mg/day os |
|---|---|---|---|---|
| 60 days Blood-chemistry tests | 30 days Blood-chemistry tests | 30 days Blood-chemistry tests | 30 days Blood-chemistry tests | 30 days Blood-chemistry tests |

TABLE 2

Statistical analysis of results

| Time | Propionyl L-carnitine | Simvastatin | Propionyl L-carnitine + simvastatin |
|---|---|---|---|
| Cholesterolaemia | | | |
| 0 | — | — | — |
| 30 days | $p < 0.4795$ | $p < 0.0585$ | $p < 0.0389$ |
| 60 days | $p < 0.0198$ | — | — |

TABLE 2-continued

Statistical analysis of results

| Time | Propionyl L-carnitine | Simvastatin | Propionyl L-carnitine + simvastatin |
|---|---|---|---|
| Triglyceridaemia | | | |
| 0 | — | — | — |
| 30 days | $p < 0.3671$ | $p < 0.0247$ | $p < 0.0015$ |
| 60 days | $p < 0.0272$ | — | — |

Results

Owing to the low dose of simvastatin and the substantial non-toxicity of propionyl L-carnitine, no side effects attributable to the drugs used were detected during the study period. All patients completed the study according to the procedures described. As regards triglyceridaemia during the period of treatment with propionyl L-carnitine, only a slight, statistically non-significant reduction ($p<0.3671$) was recorded after 30 days as compared to baseline values and this reduction proved statistically significant ($p<0.0272$) only after 60 days treatment with propionyl L-carnitine. During the wash-out period the mean triglyceridaemia value recorded was $202.5 \pm 9.71$ mg %, whereas the mean baseline value was $213.0 \pm 21.11$ mg % (Table 2).

After treatment with sirnvastatin a statistically significant reduction in triglycerides was recorded as compared to basal values ($p<0.024$), with a mean post-treatment triglyceride value of $193.8 \pm 22.63$ mg % (Table 2).

At the end of the wash-out period following simvastatin treatment, the mean triglyceride value was $205.37 \pm 13.98$ mg %. At the end of the treatment with propionyl L-carnitine and simvastatin administered simultaneously, the mean triglyceride value was $146.62 \pm 27.93$ mg % and presented a statistically significant reduction as compared to baseline conditions ($p<0,0001$). On comparing statistically the triglyceridaemia values recorded after treatment with propionyl L-carnitine and simvastatin, respectively, administered alone, with those recorded after treatment with the combination, the following significance values were found: $p<0.167$ (propionyl L-carnitine vs simvastatin); $p<0.00031$ (propionyl L-carnitine vs propionyl L-carnitine+simvastatin); $p<0.0004$ (simvastatin vs propionyl L-carnitine+simvastatin) (Table 2).

As regards cholesterolaemia values, which were within normal limits in baseline conditions (mean $158.12 \pm 25.90$ mg %), statistically significant reductions were recorded in the comparison among values recorded at the end of the first wash-out period ($158.37 \pm 25.90$ mg %), after treatment with simvastatin ($156.75 \pm 22.82$) and in the comparison between baseline values ($158.12 \pm 25.90$ mg %) and those obtained after the period of treatment with the combination of propionyl L-carnitine and simvastatin ($135.51 \pm 15.2$ mg %) ($p<0.0038$) (Table 2).

The results of this clinical study provide significant evidence in support of the enhanced effect of alkanoyl L-carnitine and statin, which constitutes the basis of the present invention. The data obtained, in fact, demonstrate without doubt that the pharmacological combination of propionyl L-carnitine and simvastatin presents a superior cholesterolaemia-lowering and triglyceridaemia-lowering effect as compared to the administration of propionyl L-carnitine and simvastatin separately and independently. This allows a drastic reduction in the daily dose of simvastatin (from 10 mg/day to 5 mg/day), which thus falls below the threshold at which the above-mentioned unwanted toxic and side effects usually manifest themselves.

What is claimed is:

1. An orally or parentally administerable pharmaceutical composition which consists essentially of synergistic effective amounts of propionyl L-carnitine or a pharmaceutically acceptable salt thereof and simvastatin in a pharmaceutically acceptable carrier or diluent.

2. A method of treating abnormalities in lipid metabolism comprising administering to a patient in need of same a lipid metabolism correcting amount of an orally or parentally administerable pharmaceutical composition which consists essentially of synergistic effective amounts of propionyl L-carnitine or a pharmaceutically acceptable salt thereof and simvastatin in a pharmaceutically acceptable carrier or diluent.

* * * * *